United States Patent
Sporn

(10) Patent No.: US 8,729,120 B2
(45) Date of Patent: May 20, 2014

(54) ADJUNCTIVE THERAPY FOR DEPRESSION

(75) Inventor: Jonathan Sporn, Princeton, NJ (US)

(73) Assignee: SK Biopharmaceuticals Co., Ltd., Seoul (KR)

( * ) Notice: Subject to any disclaimer, the term of this patent is extended or adjusted under 35 U.S.C. 154(b) by 1446 days.

(21) Appl. No.: 11/666,521

(22) PCT Filed: Oct. 26, 2005

(86) PCT No.: PCT/US2005/038804
§ 371 (c)(1),
(2), (4) Date: Aug. 6, 2007

(87) PCT Pub. No.: WO2006/050037
PCT Pub. Date: May 11, 2006

(65) Prior Publication Data
US 2008/0039529 A1    Feb. 14, 2008

Related U.S. Application Data

(60) Provisional application No. 60/623,044, filed on Oct. 28, 2004.

(51) Int. Cl.
| A61K 31/27 | (2006.01) |
| A61K 31/135 | (2006.01) |
| A61K 31/55 | (2006.01) |
| A61K 31/335 | (2006.01) |

(52) U.S. Cl.
USPC ........... 514/479; 514/649; 514/656; 514/217; 514/450

(58) Field of Classification Search
USPC .................... 514/479, 649, 656, 217, 450
See application file for complete search history.

(56) References Cited

U.S. PATENT DOCUMENTS

| 5,955,499 A * | 9/1999 | Choi et al. ............... 514/489 |
| 6,627,653 B2 | 9/2003 | Plata-Salaman |
| 2006/0154938 A1 | 7/2006 | Kikuchi |

FOREIGN PATENT DOCUMENTS

| JP | 11-501617 | 2/2001 |
| JP | 11-503447 | 3/2001 |
| JP | 2004-505043 | 2/2004 |
| JP | 2004-217650 | 8/2004 |
| WO | WO 96/07637 A | 3/1996 |
| WO | WO 96/24577 A | 8/1996 |
| WO | WO 96/32375 A | 10/1996 |

OTHER PUBLICATIONS

Belikov V. G. Pharmaceutical Chemistry, Moscow, Vysshaya Shkola, 1993, vol. 1, pp. 43-47.
Sheider R. Psychiatry, Moscow, Praktika, 1998, 293-316.
International Search Report dated Mar. 20, 2006.
Japanese Office Action, issued on Apr. 13, 2011, in the corresponding Japanese application No. 2007-539126. (An English translation of the Japanese Office Action is also enclosed).
Effect of co-administration of fluoxetine and amantadine on immunoendocrine parameters in rats subjected to a forced swimming test, Rogoz et al, Pharmacological Reports vol. 61, pp. 1050-1060 (2009).

* cited by examiner

*Primary Examiner* — Shengjun Wang
(74) *Attorney, Agent, or Firm* — Harness, Dickey & Pierce, P.L.C.

(57) ABSTRACT

This invention is directed to a method of treating depression in a subject, comprising the step of administering a therapeutically effective amount of a conventional antidepressant and, in addition, administering to the subject a therapeutically effective amount of a compound of Formula (I) or a pharmaceutically acceptable salt or ester thereof wherein Rx is a member Rx selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms; x is an integer of 1 to 3, with the proviso that R may be the same or different when x is 2 or 3; $R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom.

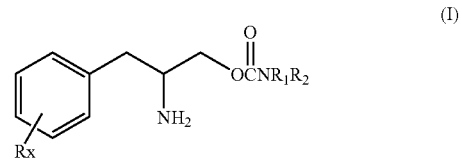

(I)

12 Claims, No Drawings

ADJUNCTIVE THERAPY FOR DEPRESSION

CROSS REFERENCE TO RELATED APPLICATIONS

This application claims the benefit of U.S. Provisional application Ser. No. 60/623,044 filed Oct. 28, 2004. This Provisional application is hereby incorporated by reference.

BACKGROUND OF THE INVENTION

1. Field of the Invention

The present invention relates generally to the fields of pharmacology, neurology and psychiatry and to methods of treating depression. More specifically, this invention provides methods for the use of certain carbamate compounds for adjunctive use in the treatment of Major Depression and related depressive disorders.

2. Description of Related Art

Major depression and depressive disorders are common illnesses that affect more than 18.8 million Americans. (See, "Depression," National Institute of Mental Health, Publication No. 00-3561 (2000)). There are several different kinds of depressive disorder Three of the more common depressive disorders include major depression, dysthymia, and bipolar disorder. Major depression is manifested by a combination of symptoms that interfere with a person's ability to function normally, including the ability to work, study, or sleep. Such disabling episodes of depression may occur only once but more commonly occur several times in a person's lifetime. Dysthymia, a less severe type of depression, involves long term chronic symptoms that do not disable a person but keep a patient from functioning well or feeling good. Bipolar disorder is a related mood disorder that is characterized by cycling mood changes from depression to manic.

Significant numbers of patients treated for depressive disorders do not respond to therapies presently available (i.e., electroconvulsive therapy (ECT), psychotherapy, and orally delivered antidepressant medications, or various combinations of all three therapies). Specifically, many patients do not respond to a single treatment modality such as a single antidepressant medication. This shortcoming exists despite the introduction of a variety of new more specific and significantly safer medications to the market place (e.g., Prozac®, Zoloft®, Paxil®). Approximately 20-30% of patients treated for depression with antidepressant medications fall into the category of being treatment-resistant and do not respond to the use of one of these agents. Janicak, P. G. and Martis, B. (1998), "Strategies for Treatment-Resistant Depression," Clinical Cornerstone 1:58-71; Shelton, R. C. (1999), "Treatment Options for Refractory Depression," J Clin. Psychiatry 60:57-63; Joffe, R. T. (1997), "Refractory Depression: Treatment Strategies, with Particular Reference to the Thyroid Axis," J. Psychiatry Neurosci. 22:327-331.

Moreover, 30% to 50% of patients do not respond to their initial medication regardless of which class of drug is chosen. The treatment-resistant population consists of patients who have been treated unsuccessfully with multiple drug trials using different classes of orally administered antidepressants, psychotherapy, and potentially ECT.

A method of treatment for patients who have failed to respond to several classes of therapeutics used alone is ECT. Unfortunately, ECT by itself, also has a failure rate of approximately 30-40%. Walter, G., Rey, J. M., and Mitchell, P. B. (1999), "Practitioner Review: Electroconvulsive Therapy in Adolescents," J Child Psychiatr 40: 325-334. ECT is a therapy that has been steadily increasing in use despite the stigma associated with its historical misuse in psychiatric medicine. ECT is now generally accepted by the American Psychiatric Association and the National Institute of Mental Health as being a safe and effective therapy for major depression. The side effects associated with ECT are generally mild and include headache, myalgia, nausea, memory problems, and confusion. Walter, G., Rey, J. M., and Mitchell, P. B. (1999), "Practitioner Review: Electroconvulsive Therapy in Adolescents," J Child Psychiatr 40: 325-334.

Unfortunately, a small percentage of the ECT-treated patients experience significant cognitive impairments (pre- and/or post treatment memory deficits of durations of weeks to months), manic switching, and tachycardia such that treatment most be discontinued. In addition, ECT requires general anesthesia and a typical course of 8-12 treatments (each treatment takes approximately 15 minutes) administered bi- or tri-weekly. Perhaps the most discouraging aspect of ECT is that greater than half of the successfully treated ECT patients will relapse into clinical depression in less than a year. Sackeim, H. A., Prudic, J., Devanand, D. P., Decina, P., and Malitz, S. (1990), "The Impact of Medication Resistance and Continuation Pharmacotherapy on Relapse Following Response to Electroconvulsive Therapy in Major Depression," J Clin Psychopharmacol 10: 96-104.

Nefazodone, a newer AD, inhibits both 5-HT 2 and 5-HT3 receptors. These antidepressive mechanisms suggest that activation of 5-HT2 and 5-HT3 receptors are not involved in the same biochemical pathways associated with selective serotonin reuptake inhibitor (SSRI)-induced efficacy. The antidepressive effects of SSRIs appears to involve 5-HT1 receptors (1A, 1B, and 1D); insomnia and sexual dysfunction effects have been attributed to 5-HT2 receptor activation and GI side effects have been attributed to 5-HT 3 receptor activation. Thase, M. E., Frazer, A., Gorman, J. M., Hirschfeld, R. M. and Roose, S. P., (2000), "Pharmacotherapy of Depression: New Strategies," A Symposium of the American Psychiatric Association 2000 Annual Meeting.

The majority of antidepressants presently used are designed to affect one or both of the two major neurotransmitter systems of the brain, norepinephrine and serotonin. Antidepressants inhibit the neuronal reuptake (tricyclic antidepressants—norepinephrine (NE) and 5-HT, SSRIs—just 5-HT, selective norepinephrine reuptake inhibitors—just NE) or degradation (monoamine oxidase inhibitors) of one or both of these neurotransmitters. Although this is the common "first step" pharmacologic effect of antidepressants that leads to a corresponding increase in synaptic neurotransmitter concentrations, the precise biochemical pathways which lead to the ultimate therapeutic outcome have yet to be elucidated. It also is not appreciated why this pharmacologic first step occurs almost immediately after the medication is taken, whereas the patient does not experience relief from his/her symptoms of depression for weeks afterwards.

Recent theories proposed on the biochemical mechanisms of antidepressants (ADs) focus on adrenoceptors and the enzyme responsible for NE synthesis, tyrosine hydroxylase. Leonard, B. E., (1997), "Noradrenaline in Basic Models of Depression," Eur Neuropsychopharmacol 7: 511-516. Many ADs produce a decrease in function and/or adrenoceptor density as well as decreases in the tyrosine hydroxylase levels in the brain. Thase, M. E., Frazer, A., Gorman, J. M., Hirschfeld, R. M. and Roose, S. P., (2000), "Pharmacotherapy of Depression: New Strategies," A Symposium of the American Psychiatric Association 2000 Annual Meeting.

Thus the traditional ADs are limited by the endogenous pool of NE available in the vesicles of the nerve terminals. Those skilled in the art will realize that in pharmacology drugs that exert their effects indirectly (i.e., are dependent on the causing the release of or inhibiting the degradation of a primary endogenous molecule) are usually limited in the maximum effect they can produce. This efficacy limitation is a direct result of the limited pool of endogenous agonist. It is also conceivable that the lack of an adequate clinical response to oral reuptake inhibitors in select patient populations is a result of depleted or inaccessible pools of NE within the terminals of the presynaptic neurons. It is reasonable to assume that only with an intact endogenous supply of presynaptic NE can the initial pharmacologic impact of reuptake inhibition be expected to occur. Since this supply must be limited it is likely that in most cases the use of two or more medications or treatment that do not act on the same neurotransmitter system could be expected to have at least additive and very possibly synergistic effects. This positive therapeutic effect would not be expected to be as limited by the availability of one neurotransmitter because it would rely on multiple pathways and neurotransmitters Thus there is a need to discover compounds having independent antidepressant action but that have atypical mechanisms of action. These compounds could be used in combination with conventional antidepressants that effect serotonin and norepinephrine receptors or neurotransmission and provide enhanced efficacy.

SUMMARY OF THE INVENTION

The present invention is directed to a method of treating depression in a subject, comprising the step of the concomitant administration, to a subject in need of such treatment, of a therapeutically effective amount of a conventional antidepressant and a therapeutically effective amount a compound of the Formula (I):

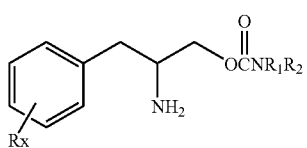

(I)

or a pharmaceutically acceptable salt or ester thereof wherein
Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;
x is an integer of 1 to 3, with the proviso that R may be the same or different when x is 2 or 3;
$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom.

Embodiments of the invention include a method of treating depression in a subject, comprising the step of the concomitant administration, to a subject in need of such treatment, of a therapeutically effective amount of a conventional antidepressant and a therapeutically effective amount an enantiomer of Formula I substantially free of other enantiomers or an enantiomeric mixture wherein one enantiomer of Formula I predominates;

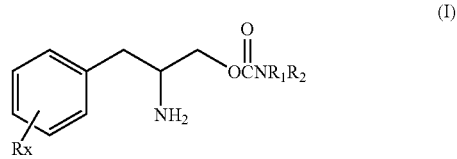

(I)

or a pharmaceutically acceptable salt or ester thereof wherein
Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;
x is an integer of 1 to 3, with the proviso that R may be the same or different when x is 2 or 3;
$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom. Preferably, wherein Rx, R1 and R2 are all selected from hydrogen. Preferably wherein one enantiomer selected from the group consisting of Formula I predominates to the extent of about 90% or greater.

More preferably, wherein one enantiomer selected from the group consisting of Formula 1 predominates to the extent of about 98% or greater.

Embodiments of the invention include a method for using the enantiomer selected from the group consisting of Formula I for the preparation of a medicament for adding to a conventional antidepressant for the treatment of depression.

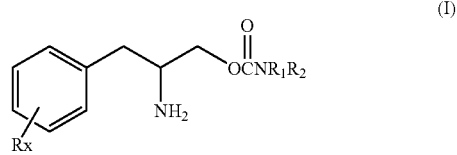

(I)

or a pharmaceutically acceptable salt or ester thereof wherein
Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms;
x is an integer of 1 to 3, with the proviso that R may be the same or different when x is 2 or 3;
$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 1 to 2 nitrogen atoms and 0 to 1 oxygen atom, wherein the nitrogen atoms are not directly connected with each other or with the oxygen atom.

Embodiments of the invention include a method include the use of the enantiomer of Formula I substantially free of other enantiomers that is the enantiomer of Formula Ib or an enantiomeric mixture wherein the enantiomer of Formula Ib predominates.

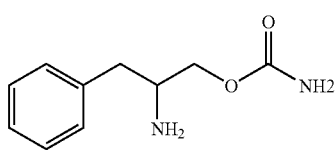

Formula Ib wherein the enantiomer of Formula 1b predominates to the extent of about 90% or greater. More preferably, an enantiomer of Formula 1b predominates to the extent of about 98% or greater.

Embodiments of the invention include a methods wherein the conventional antidepressant is chosen from the group consisting of; selective serotonin reuptake inhibitors (SSRI's); selective serotonin and norepinephrine reuptake inhibitors (SNRI's); older tricyclic antidepressants (TCAs); monoamine oxidase inhibitors (MAO-inhibitors), reversible inhibitors of monoamine oxidase (RIMAs), tertiary amine tricyclics and secondary amine tricyclic antidepressants Embodiment of the invention include a method wherein the conventional antidepressant is chosen from the group consisting of; fluoxetine, duloxetine, venlafaxine, milnacipran, citalopram, fluvoxamine, paroxetine, sertraline, 5-MCA-NAT, lithium carbonate (liCO3), isocarboxazid, phenelzine, tranylcypromine, selegiline, moclobemide, kappa opioid receptor antagonists; selective neurokinin antagonists, corticotropin releasing factor (CRF) antagonists, antagonists of tachykinins, α-adrenoreceptor antagonists. amitriptyline, clomipramine, doxepin, imipramine,: venlafaxine, trimipramine, amoxapine, desipramine, maprotiline, nortriptyline and protriptyline, and pharmaceutically acceptable salts thereof and wherein the therapeutically effective amount of enantiomer is from about 0.01 mg/kg/dose to about 300 mg/kg/dose.

DETAILED DESCRIPTION OF THE INVENTION

The present invention is based in part on the discovery that phenylalkylamino carbamates of Formula I have novel and unique pharmacological properties. These compounds have been shown in both animal models and in studies in humans to have anti-depressant action and to have an activating or energizing effect. Although the precise mechanism of action is not completely understood it is known that these compounds do not work as antidepressants by the same mechanisms as most other known antidepressants. For these two reasons the compounds of Formula I are especially suitable for use as adjunctive treatment for depression. Thus, these compounds can be safely used in combination with these older drugs to provide enhanced efficacy and reduced side effects because of the smaller doses of each drug that can be used.

Therefore in the methods of this invention these carbamate compounds can be added or combined in a regimen with one or more other conventional antidepressants to produce a combination with, in some embodiments, increased therapeutic efficacy and, in some embodiments, reduced toxicity because of the use of lower doses of each component than would be required if each therapeutic agent was used alone. Thus, in some embodiments of this invention, the subject or patient is already stabilized on the conventional antidepressant but may be showing only a partial response. In this embodiment, the compound of Formula I is added to the existing regimen in doses of 1.0 mg to 100.00 mg/day increments until a more complete response is achieved or unacceptable side effects occur. One of skill in the art can assess response through clinical interviews or questionnaires that measure depressive symptoms such as the Ham-D, etc.

In other embodiments, the conventional antidepressant in started simultaneously with the compound of Formula I; this is concomitant administration. In this embodiment the conventional antidepressant would be started at smaller than recommended starting doses for single compound treatment, for example starting doses of 5.0 mg/day to 20.0 mg/day for an SSRI or 25 mg/day to 50 mg/day for a tricyclic antidepressant such as imipramine. One of skill in the art could readily determine appropriate doses of conventional antidepressant from the manufactures recommendations and the side effects experienced by the patient.

In embodiments in which both antidepressants are started simultaneously the doses of compounds of Formula I would be determined by side effects and response. Typically, doses of a compound of Formula I would start at 25-50 mg/day and increase in increments of about 25 -50 mg./day per week until side effects intervene or an adequate response is obtained. One compound of Formula I, (referred to herein as the "test compound"), is (R)-(beta-amino-benzenepropyl) carbamate monohydrochloric acid

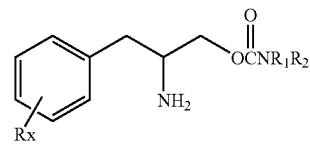

wherein Rx=R1=R2=hydrogen. This compound has been tested in numerous animal models and in humans and has demonstrated antidepressant effects, these models include; Reserpine Reversal in Mice, Tetrabenazine Reversal in Mice, Reversal of Isolation-Induced Aggression in Mice, Tail Suspension in Mice and the Forced-Swim Test (FST) in Mice and Rats. The compounds show stimulant or energizing effects in the Spontaneous Locomotor Activity in Mice and Rats model.

In humans, the test compound has shown significant antidepressant effects in a large placebo controlled study where it was compared with a conventional SSRI antidepressant (Paroxetine) See Table 1

TABLE 1

PRIMARY EFFICACY RESULTS (ITT):
CHANGE IN TOTAL MADRS BY WEEK (depression rating scale)
PRIMARY EFFICACY RESULTS - MADRS (ITT.LOCF)

| Change from Baseline | PLACEBO (N-117) | Test Compound 200 mg (N-115) | Test Compound 400 mg (N-120) | Paroxetine 20 mg (N-120) |
|---|---|---|---|---|
| Mean (SD) | −10.3 (10.19) | −12.1 (11.12) | −12.4 (11.12) | −14.1 (10.71) |
| P-Value (adjusted) | | 0.118 | 0.112 | |
| P-Value | | | | 0.001 |

Table 1 shows that treatment with test compound produced a greater decrease in depression rating scores (MADRS) as compared to placebo but not as great as the active control, paroxetine.

Thus in some embodiments, the present invention is directed to a method of adjunctive treatment of depression. The term "adjunctive treatment of depression" as used herein means the addition or combination of the compounds of the present invention with one or more conventional antidepressants in order to enhance the efficacy of the conventional antidepressant and/or allow lower doses of the conventional antidepressant thus reducing side effects while enhancing the efficacy of the conventional antidepressant in treating depression or preventing the reoccurrence of depression. The method comprising administering to a subject in need thereof a therapeutically effective amount of a conventional antidepressant in combination with a therapeutically effective amount of a compound selected from the group consisting of phenylalkylamino carbamates of the following Formula I:

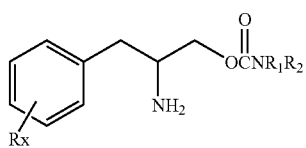

Formula I or an enantiomer, diastereomer, racemate or mixtures thereof, or a pharmaceutically acceptable salt or ester thereof wherein;

Rx is a member selected from the group consisting of hydrogen, lower alkyl of 1 to 8 carbon atoms, halogen selected from F, Cl, Br and I, alkoxy containing 1 to 3 carbon atoms, nitro, hydroxy, trifluoromethyl, and thioalkoxy containing 1 to 3 carbon atoms; x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms; $R_1$ and $R_2$ can be joined to form a 5 to 7-membered heterocycle substituted with a member selected from the group consisting of hydrogen, alkyl, and aryl groups, wherein the cyclic compound can comprise 0 to 2 nitrogen atoms and 0 to 1 oxygen atoms, wherein the nitrogen atoms are not directly connected with each other or with the oxygen atom and the pharmaceutically acceptable salts and esters thereof.

The present method also includes the use of a compound selected from the group consisting Formula I wherein Rx, R1 and R2 are preferably selected from hydrogen, this is Formula Ia below;

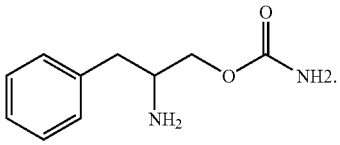

Formula Ia

The present method also includes the use of the D enantiomer selected from the group consisting of Formula I or an enantiomeric mixture wherein the D enantiomer selected from the group consisting of Formula Ia predominates wherein Rx, R1 and R2 are preferably selected from hydrogen, this is O-carbamoyl-(D)-phenylalaninol. Formula Ib below;

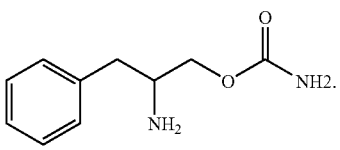

Formula Ib

For enantiomeric mixtures wherein one enantiomer selected from the group consisting of Formula I predominates, preferably, an enantiomer selected from the group consisting of Formula I predominates to the extent of about 90% or greater. More preferably, an enantiomer selected from the group consisting of Formula 1 predominates to the extent of about 98% or greater.

The compounds of Formula I can be synthesized by methods known to a skilled artisan. Some reaction schemes for synthesizing compounds of Formula (I) have been described in U.S. Pat. Nos. 5,705,640, 5,756,817, 5,955,499, and 6,140,532. All of these patents are hereby incorporated by reference in their entirety.

The salts and esters of the compounds of Formula (I) can be produced by treating the compound with an acid (HX) in suitable solvent or by means well known to those of skill in the art.

Details of the above reactions schemes as well as representative examples on the preparation of specific compounds have been described in U.S. Pat. Nos. 5,705,640, 5,756,817, 5,955,499, 6,140,532, all incorporated herein by reference in their entirety.

From Formula I it is evident that some of the compounds of the invention have at least one and possibly more asymmetric carbon atoms. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known from the art.

As used herein the term "conventional antidepressant" shall mean any compound known to possess antidepressant action in mammals that can be used in combination with the carbamate compounds of the present invention. Thus, the term includes but is not limited to: selective serotonin reuptake inhibitors (SSRI's); selective serotonin and norepinephrine reuptake inhibitors (SNRI's); older tricyclic antidepressants; bupropion and MAO inhibitors.

Selective serotonin reuptake inhibitors (SSRI's) and selective serotonin and norepinephrine reuptake inhibitors (SNRI's) include, but are not limited to:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., J. Med. Chem, 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers;

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and U.S. Pat No. 4,761,501 teaches its method of synthesis and its activity as an inhibitor of serotonin and norepinephrine uptake. Venlafaxine is identified as compound A in that patent.

Milnacipran (N, N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., Neuropharmacology 24, 1211-19 (1985), describe its pharmacological activities as an inhibitor of serotonin and norepinephrine reuptake;

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen et al., Eur. J Pharmacol. 41, 153 (1977), and reports of its clinical effectiveness in depression may be found in Dufour et al., Int. Clin. Psychopharmacol. 2, 225 (1987), and Timmerman et al., ibid., 239;

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen et al., Brit. J. Pharmacol. 60, 505 (1977); and De Wilde et al., J. Affective Disord. 4, 249 (1982); and Benfield et al., Drugs 32, 313 (1986);

Paroxetine, trans-(-)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, Eur. J. Pharmacol. 47, 351 (1978); Hassan et al., Brit J. Clin. Pharmacol. 19, 705 (1985); Laursen et al., Acta Psychiat. Scand. 71, 249 (1985); and Battegay et al., Neuropsychobiology 13, 31 (1985); and Sertraline, (1S-cis)-4-(3,4-dichlorophenyl)-1,2,3,4-tetrahydro-N-methyl-1-naphthylamine hydrochloride, is a serotonin reuptake inhibitor that is marketed as an antidepressant. It is disclosed by U.S. Pat. No. 4,536,518.

Carbamate compounds of the present invention may also be used in combination with other classes of antidepressants including but not limited to other therapeutically effective agents, for example; 5-MCA-NAT (e.g., U.S. Pat. No. 6,562,858); lithium carbonate (liCO3), monoamine oxidase inhibitors (MAO-inhibitors), suitable monoamine oxidase inhibitors include: isocarboxazid, phenelzine, tranylcypromine and selegiline, and pharmaceutically acceptable salts thereof; reversible inhibitors of monoamine oxidase (RIMAs), suitable reversible inhibitors of monoamine oxidase include: moclobemide, and pharmaceutically acceptable salts thereof; antiepileptic drugs (AEDs) including but not limited to kappa opioid receptor antagonists (e.g., U.S. Pat. No. 6,528,518); selective neurokinin antagonists (e.g., U.S. Pat. No. 6,436,928) corticotropin releasing factor (CRF) antagonists, suitable CRF antagonists include those compounds described in International Patent Specification Nos. WO 94/13643, WO 94/13644, WO 94/13661, WO 94/13676 and WO 94/13677.; antagonists of tachykinins (e.g., U.S. Pat. No. 6,518,273) and α-adrenoreceptor antagonists.

In addition the compounds of the present invention can be used in combination with older antidepressants that are primarily norepinephrine reuptake inhibitors. Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof.

Suitable examples of secondary amine tricyclics include: amoxapine, desipramine, maprotiline, nortriptyline and protriptyline, and pharmaceutically acceptable salts thereof.

Suitable serotonin and noradrenaline reuptake inhibitors of use in the present invention include: venlafaxine, and pharmaceutically acceptable salts thereof.

Use of compounds disclosed herein and their analogs in combination with other drugs may reduce the amounts of drugs used in the treatment and thereby alleviating some of the major side effects observed. Furthermore, the period observed between administering the drugs and any observed therapeutic indications may be diminished by the combination effect.

All of the U.S. patents that have been mentioned above in connection with compounds used in the present invention are incorporated herein by reference.

Definitions

For convenience, certain terms employed in the specification, examples, and appended claims are collected here.

It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention which will be limited only by the appended claims.

As used herein, the term "mental disorder" and "mental illness" refer to those provided in the Diagnostic and Statistical Manual (DSM IV), American Psychological Association (APA). These mental disorders include, but are not limited to affective disorders, Major Depression and related depressive disorders. Examples of affective disorders include mood disorders, manic disorder, major depressive disorder and bipolar affective disorder. Mood disorders include, but are not limited to, depressive disorders including Major Depression with or without psychotic features, dysthymic disorder, bipolar disorders (I and II) and cyclothymic disorders.

As used herein the term "subject", refers to an animal, preferably a mammal, and most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated.

The term "prophylactically effective amount" is intended to mean that amount of a pharmaceutical drug that will prevent or reduce the risk of occurrence of the biological or medical event that is sought to be prevented of a tissue, a system, animal or human that is being sought by a researcher, veterinarian, medical doctor or other clinician.

The term "pharmaceutically acceptable salts or esters" shall mean non-toxic salts or esters of the compounds employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methyinitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Therefore, the term "a patient in need of treatment" as used herein will refer to any subject or patient who currently has or may develop any of the above syndromes or disorders, including any mood disorder which can be treated by antidepressant medication, or any other disorder in which the patient's present clinical condition or prognosis could benefit from the administration of one or more compounds of Formula (I) alone or in combination with another therapeutic intervention including but not limited to another medication.

The term "pharmacophore" is known in the art, and, as used herein, refers to a molecular moiety capable of exerting a selected biochemical effect, e.g., inhibition of an enzyme, binding to a receptor, chelation of an ion, and the like. A selected pharmacophore can have more than one biochemical effect, e.g., can be an inhibitor of one enzyme and an agonist of a second enzyme. A therapeutic agent can include one or more pharmacophore, which can have the same or different biochemical activities.

The term "treating" or "treatment" as used herein, refers to any indicia of success in the prevention or amelioration of an injury, pathology or condition, including any objective or subjective parameter such as abatement; remission; diminishing of symptoms or making the injury, pathology, or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of a physical examination, neurological examination, and/or psychiatric evaluations. Accordingly, the term "treating" or "treatment" includes the administration of the compounds or agents of the present invention to provide antidepressant action. In some instances, treatment with the compounds of the present invention will done in combination with other antidepressant compounds to prevent, inhibit, or arrest the progression of the mood disorder.

The term "therapeutic effect" as used herein, refers to the effective provision of antidepressant action.

The term "a therapeutically effective amount" as used herein means a sufficient amount of one or more of the compounds of the invention to produce a therapeutic effect, as defined above, in a subject or patient in need of such neuroprotection treatment.

The terms "subject" or "patient" are used herein interchangeably and as used herein mean any mammal including but not limited to human beings including a human patient or subject to which the compositions of the invention can be administered. The term mammals include human patients and non-human primates, as well as experimental animals such as rabbits, rats, and mice, and other animals.

Methods are known in the art for determining therapeutically and prophylactically effective doses for the instant pharmaceutical composition. For example, for use as an adjunct for treating depression, the compound can be employed at a daily dose in the range of about 0.1 mg to 400 mg usually on a regimen of 1 to 2 times per day, for an average adult human. The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound may be administered to a subject by any conventional route of administration, including, but not limited to, intravenous, oral, subcutaneous, intramuscular, intradermal and parenteral. Depending on the route of administration, compounds of Formula (I) can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

To prepare the pharmaceutical compositions of this invention, one or more compounds of formula (I) or salt thereof as the active ingredient is intimately admixed with a pharmaceutical carrier according to conventional pharmaceutical compounding techniques. Carriers are necessary and inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl- pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Preferably these compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 25 to about 400 mg of the active ingredient. Preferably, the range is from about 50 to about 200 mg of the active ingredient.

In some embodiments of the present invention carbamate compounds suitable for use in the practice of this invention will be administered either singly or concomitantly with at least one or more other compounds or therapeutic agents, e.g., with other antidepressant agents. In these embodiments, the present invention provides methods to treat or prevent depression in a patient. The method includes the step of; administering to a patient in need of treatment, an effective amount of one of the carbamate compounds disclosed herein in combination with an effective amount of one or more other compounds or therapeutic agents that have the ability to provide antidepressant effects or the ability to augment the antidepressant effects of the compounds of the invention.

The term "concomitant administration" or "combination administration" of a compound, therapeutic agent or known drug with a compound of the present invention means administration of the conventional antidepressant and, in addition, the one or more compounds of the invention at such time that both the known drug and the compound will have a therapeutic effect. In some cases this therapeutic effect will be synergistic. Such concomitant administration can involve concurrent (i.e. at the same time), prior, or subsequent administration of the conventional antidepressant with respect to the administration of a compound of the present invention. A person of ordinary skill in the art, would have no difficulty determining the appropriate timing, sequence and dosages of administration for particular drugs and compounds of the present invention.

In addition, in some embodiments, the compounds of this invention will be used, either alone or in combination with each other or in combination with one or more other therapeutic medications as described above, or their salts or esters, for manufacturing a medicament for the purpose of providing adjuvant antidepressants action to a patient or subject in need thereof.

The term, "$C_1$-$C_4$ alkyl" as used herein refers to substituted or unsubstituted aliphatic hydrocarbons having from 1 to 4 carbon atoms. Specifically included within the definition of "alkyl" are those aliphatic hydrocarbons that are optionally substituted. In a preferred embodiment of the present invention, the $C_1$-$C_4$ alkyl is either unsubstituted or substituted with phenyl.

The term "phenyl", as used herein, whether used alone or as part of another group, is defined as a substituted or unsubstituted aromatic hydrocarbon ring group having 6 carbon atoms. Specifically included within the definition of "phenyl" are those phenyl groups that are optionally substituted. For example, in a preferred embodiment of the present invention, the, "phenyl" group is either unsubstituted or substituted with halogen, $C_1$-$C_4$ alkyl, $C_1$-$C_4$ alkoxy, amino, nitro, or cyano.

It is understood that substituents and substitution patterns on the compounds of the present invention can be selected by one of ordinary skill in the art to provide compounds that are chemically stable and that can be readily synthesized by techniques known in the art as well as the methods provided herein.

Representative 2-phenyl-1,2-ethanediol monocarbomates and dicarbamates include, for example, the following compounds:

The present invention includes the use of isolated enantiomers of Formula 1. In one preferred embodiment, a pharmaceutical composition comprising the isolated S-enantiomer of Formula 1 is used to provide adjuvant antidepressant efficacy in a subject. In another preferred embodiment, a pharmaceutical composition comprising the isolated R-enantiomer of Formula 1 is used to provide adjuvant antidepressant efficacy a subject The present invention also includes the use of mixtures of enantiomers of Formula 1. In one aspect of the present invention, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one preferred embodiment, the enantiomer that predominates in a composition comprising a compound of Formula 1 is the S-enantiomer of Formula 1.

The present invention provides methods of using enantiomers and enantiomeric mixtures of compounds represented by Formula 1. A carbamate enantiomer of Formula 1 contains an asymmetric chiral carbon at the benzylic position, which is the second aliphatic carbon adjacent to the phenyl ring.

An enantiomer that is isolated is one that is substantially free of the corresponding enantiomer. Thus, an isolated enantiomer refers to a compound that is separated via separation techniques or prepared free of the corresponding enantiomer. The term "substantially free," as used herein, means that the compound is made up of a significantly greater proportion of one enantiomer. In preferred embodiments, the compound includes at least about 90% by weight of a preferred enantiomer. In other embodiments of the invention, the compound includes at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein.

Carbamate Compounds as Pharmaceuticals:

The present invention provides racemic mixtures, enantiomeric mixtures and isolated enantiomers of Formula 1 as pharmaceuticals. The carbamate compounds are formulated as pharmaceuticals to provide adjuvant antidepressant action in a subject.

In general, the carbamate compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intacerebroventricular, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso AR: *Remington's Pharmaceutical Sciences,* 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The carbamate compounds can be provided as aqueous suspensions. Aqueous suspensions of the invention can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol monooleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be and is preferably administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 50 % w of the carbamate compound, preferably 0.00001 % w to 25% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Formulations suitable for oral administration can consist of (a) liquid solutions, such as an effective amount of the pharmaceutical formulation suspended in a diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropyl-methyl-cellulose or sodium carboxymethylcellulose; and gums including arabic and tragacanth; as well as proteins such as gelatin and collagen.

If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention.

In another embodiment, the compounds of the present invention can be delivered by the use of liposomes which fuse with the cellular membrane or are endocytosed, i.e., by employing ligands attached to the liposome that bind to surface membrane protein receptors of the cell resulting in endocytosis. By using liposomes, particularly where the liposome surface carries ligands specific for target cells, or are otherwise preferentially directed to a specific organ, one can focus the delivery of the carbamate compound into target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5, that is combined with buffer prior to use.

Pharmaceutically acceptable salts and esters refers to salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds. When there are two acidic groups present, a pharmaceutically acceptable salt or ester may be a mono-acid-mono-salt or ester or a di-salt or ester; and similarly where there are more than two acidic groups present, some or all of such groups can be salified or esterified.

Compounds named in this invention can be present in unsalified or unesterified form, or in salified and/or esterified form, and the naming of such compounds is intended to include both the original (unsalified and unesterified) compound and its pharmaceutically acceptable salts and esters. The present invention includes pharmaceutically acceptable salt and ester forms of Formula (1). More than one crystal form of an enantiomer of Formula 1 can exist and as such are also included in the present invention.

A pharmaceutical composition of the invention can optionally contain, in addition to a carbamate compound, at least one other therapeutic agent useful in the treatment of depression or other mood disorder. For example the carbamate compounds of Formula 1 can be combined physically with other antidepressants in fixed dose combinations to simplify their administration.

Methods of formulating pharmaceutical compositions have been described in numerous publications such as *Pharmaceutical Dosage Forms: Tablets*. Second Edition. Revised and Expanded. Volumes 1-3, edited by Lieberman et al; *Pharmaceutical Dosage Forms*: Parenteral Medications. Volumes 1-2, edited by Avis et al; and *Pharmaceutical Dosage Forms: Disperse Systems*. Volumes 1-2, edited by Lieberman et al; published by Marcel Dekker, Inc, the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Dosage Regimens

The present invention provides methods of providing adjuvant antidepressant action in a mammal using carbamate compounds. The amount of the carbamate compound necessary to provide adjuvant antidepressant action is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of ordinary skill in the art will be able without undue experimentation, having regard to that skill and this disclosure, to determine a therapeutically effective amount of a particular substituted carbamate compound for practice of this invention (see, e.g., Lieberman, Pharmaceutical Dosage Forms (Vols. 1-3, 1992); Lloyd, 1999, The art, Science and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to provide antidepressant action. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

The active compound present in these unit dosage forms of the composition can be present in an amount of, for example, from about 10 mg to about one gram or more, for single or multiple daily administration, according to the particular need of the patient. By initiating the treatment regimen with a minimal daily dose of about one gram, the blood levels of the carbamate compounds can be used to determine whether a larger or smaller dose is indicated.

Effective administration of the carbamate compounds of this invention can be administered, for example, at an oral or parenteral dose of from about 0.01 mg/kg/dose to about 150 mg/kg/dose. Preferably, administration will be from about 0.1/mg/kg/dose to about 25 mg/kg/dose, more preferably from about 0.2 to about 18 mg/kg/dose. Therefore, the therapeutically effective amount of the active ingredient contained per dosage unit as described herein can be, for example, from about 1 mg/day to about 7000 mg/day for a subject having, for example, an average weight of 70 kg.

The methods of this invention also provide for kits for use in providing adjuvant antidepressant action. After a pharmaceutical composition comprising one or more carbamate compounds of this invention, with the possible addition of one or more other compounds of therapeutic benefit, has been formulated in a suitable carrier, it can be placed in an appropriate container and labeled for providing adjuvant antidepressant action. Additionally, another pharmaceutical comprising at least one other therapeutic agent useful in the provide antidepressant action can be placed in the container as well and labeled for treatment of the indicated disease. Such labeling can include, for example, instructions concerning the amount, frequency and method of administration of each pharmaceutical.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation. The following examples are provided to illustrate specific aspects of the invention and are not meant to be limitations.

References Cited

All references cited herein are incorporated herein by reference in their entirety and for all purposes to the same extent as if each individual publication or patent or patent application was specifically and individually indicated to be incorporated by reference in its entirety for all purposes.

The discussion of references herein is intended merely to summarize the assertions made by their authors and no admission is made that any reference constitutes prior art. Applicants reserve the right to challenge the accuracy and pertinence of the cited references.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein will be apparent to those skilled in the art from the foregoing description and accompanying drawings. Such modifications and variations are intended to fall within the scope of the appended claims. The present invention is to be limited only by the terms of the appended claims, along with the full scope of equivalents to which such claims are entitled.

What is claimed is:

1. A method for treating depression in a subject comprising:
administering to a subject in need of such treatment a therapeutically effective amount of an antidepressant selected from the group consisting of fluoxetine, amitriptyline, clomipramine, doxepin, imipramine, trimipramine and a pharmaceutically acceptable salt thereof in combination with a therapeutically effective amount of a compound of Formula Ib:

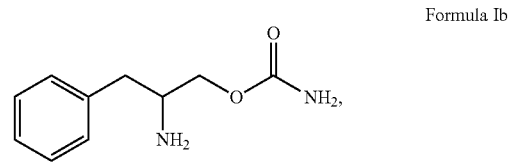 [SMILES: NC(=O)OCC(N)Cc1ccccc1]

Formula Ib or a pharmaceutically acceptable salt thereof.

2. The method of claim 1, wherein the compound of Formula Ib is an enantiomer.

3. The method of claim 2, wherein the enantiomer is a (D) enantiomer.

4. The method of claim 3, wherein the (D) enantiomer predominates to the extent of about 90% or greater.

5. The method of claim 3, wherein the (D) enantiomer predominates to the extent of about 98% or greater.

6. The method of claim 1, wherein the antidepressant is fluoxetine or amitriptyline.

7. The method of claim 1, wherein the method reduces a side effect of the antidepressant.

8. The method of claim 1, wherein the antidepressant is administered at a dose smaller than a recommended starting dose.

9. The method of claim 1, wherein the therapeutically effective amount of the compound of Formula lb is from about 0.01 mg/kg/dose to about 300 mg/kg/dose.

10. The method of claim 1, wherein the compound of Formula lb is administered at a dose of from 1.0 mg/day to about 100.00 mg/day.

11. The method of claim 1, wherein the compound of Formula Ib is administered orally or parenterally.

12. The method of claim 1, wherein the compound of Formula Ib is administered in a form of tablet.

* * * * *